(12) United States Patent
Stinson

(10) Patent No.: US 7,972,375 B2
(45) Date of Patent: Jul. 5, 2011

(54) ENDOPROSTHESES INCLUDING METAL MATRIX COMPOSITE STRUCTURES

(75) Inventor: Jonathan S. Stinson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 647 days.

(21) Appl. No.: 11/671,256

(22) Filed: Feb. 5, 2007

(65) Prior Publication Data
US 2008/0188922 A1 Aug. 7, 2008

(51) Int. Cl.
A61F 2/06 (2006.01)
(52) U.S. Cl. ............................ 623/1.44; 623/1.45
(58) Field of Classification Search ................. 623/1.15, 623/1.18, 1.32, 1.34, 1.45, 1.49
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 4,668,290 A | 5/1987 | Wang et al. | |
| 5,195,969 A | 3/1993 | Wang et al. | |
| 5,238,004 A | 8/1993 | Sahatjian et al. | |
| 5,270,086 A | 12/1993 | Hamlin | |
| 5,366,504 A | 11/1994 | Andersen et al. | |
| 5,674,242 A | 10/1997 | Phan et al. | |
| 5,780,807 A | 7/1998 | Saunders | |
| 5,800,511 A | 9/1998 | Mayer | |
| 5,888,201 A | 3/1999 | Stinson et al. | |
| 6,287,331 B1 | 9/2001 | Heath | |
| 6,364,902 B1 | 4/2002 | Dickenson et al. | |
| 6,508,803 B1 | 1/2003 | Horikawa et al. | |
| 6,726,712 B1 | 4/2004 | Raeder-Devens et al. | |
| 7,029,495 B2 | 4/2006 | Stinson | |
| 2001/0047185 A1 | 11/2001 | Satz | |
| 2003/0018381 A1* | 1/2003 | Whitcher et al. | 623/1.15 |
| 2004/0044397 A1 | 3/2004 | Stinson | |
| 2004/0158309 A1* | 8/2004 | Wachter et al. | 623/1.13 |
| 2005/0051243 A1 | 3/2005 | Forbes Jones et al. | |
| 2005/0159806 A1* | 7/2005 | Shanley | 623/1.15 |
| 2005/0261760 A1* | 11/2005 | Weber | 623/1.38 |
| 2006/0161256 A1* | 7/2006 | Ziegler et al. | 623/11.11 |
| 2006/0200224 A1* | 9/2006 | Furst et al. | 623/1.15 |
| 2007/0207186 A1* | 9/2007 | Scanlon et al. | 424/424 |
| 2008/0160259 A1* | 7/2008 | Nielson et al. | 428/148 |

FOREIGN PATENT DOCUMENTS

| | | |
|---|---|---|
| EP | 0 586 758 | 3/1994 |
| WO | WO 2004/108021 | 12/2004 |
| WO | WO 2006/107677 | 10/2006 |

OTHER PUBLICATIONS

Garino, "Oxidized Metal Powders for Mechanical Shock and Crush Safety Enhancements," *Sandia Report*, 2002, 6 pages.
Authorized Officer Masashi Honda, International Preliminary Report on Patentability in PCT/US08/53058 mailed Aug. 20, 2009, 7 pages.

* cited by examiner

*Primary Examiner* — David Isabella
*Assistant Examiner* — Joshua Levine
(74) *Attorney, Agent, or Firm* — Fish & Richardson P.C.

(57) ABSTRACT

An endoprosthesis that includes a composite having a metal matrix and a plurality of stiffening particles in the matrix. The metal of the metal matrix can include titanium, niobium, tantalum, or alloys thereof. The stiffening particles can include a metal core and a thin surface layer. The thin surface layer can include oxides, carbides, nitrides, or combinations thereof.

23 Claims, 3 Drawing Sheets

ENDOPROSTHESES INCLUDING METAL MATRIX COMPOSITE STRUCTURES

TECHNICAL FIELD

The invention relates to composite materials for endoprostheses, such as stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly. Methods of monitoring a medical device include X-ray fluoroscopy, computed tomography (CT), and magnetic resonance imaging (MRI).

SUMMARY

An endoprosthesis is disclosed that includes a composite having a metal matrix and a plurality of stiffening particles in the matrix. The metal of the metal matrix can include titanium, niobium, tantalum, or alloys thereof. The stiffening particles can include a metal core and a thin surface layer. The thin surface layer can include oxides, carbides, nitrides, or combinations thereof. The thickness of the surface layer can be between 1 and 100 nm.

In some embodiments, the metal core of the stiffening particles can include tungsten, indium, molybdenum, tantalum, or alloys thereof. The stiffening particles can have an average particle size ranging from 0.1 µm to 10 µm. The composite can include between 10 and 35% by weight of the stiffening particles, based upon the weight of the composite. The composite can have a Young's modulus of elasticity of at least 18 Mpsi, or between 18 Mpsi and 30 Mpsi, a yield strength of between 60 and 100 ksi, a percent elongation at break of 12-30%, and/or a density of 4.5-18.0 g/cm$^3$. In some embodiments, the stiffening particles can have a Young's modulus of elasticity of at least 30 Mpsi.

In some embodiments, the endoprosthesis can be a stent. The composite-containing portion of the stent can have a wall thickness of between about 0.0015 inches and about 0.0060 inches. The stent can include one or more bands. The stent can also include a plurality of connectors connecting the bands.

A method of making an endoprosthesis is also disclosed. The method can include manufacturing microtubing from a composite that includes a metal matrix and a plurality of stiffening particles in the matrix, and machining the microtubing to form the endoprosthesis. The metal of the metal matrix can include titanium, niobium, tantalum, or alloys thereof. The stiffening particles can include a metal core and a thin surface layer. The thin surface layer can include oxides, carbides, nitrides, or combinations thereof.

In some embodiments, the manufacturing can include subjecting the composite to pilgering, fixed mandrel drawing, floating plug drawing, or a combination thereof. The composite can be prepared by consolidating a precursor composition that includes (a) a powder comprising the metal matrix material and (b) the stiffening particles. The precursor composition can be consolidated according to a process selected from the group consisting of cold compaction, sintering, hot isostatic pressing, extrusion, and combinations thereof.

The term "particles" as used herein refers to both spherical and non-spherical shapes, including spherical shapes, irregular shapes, fibers, plates, chards, whiskers, and prolated spheres.

Other aspects, features, and advantages will be apparent from the detailed description and from the claims.

DETAILED DESCRIPTION

Figure 1:
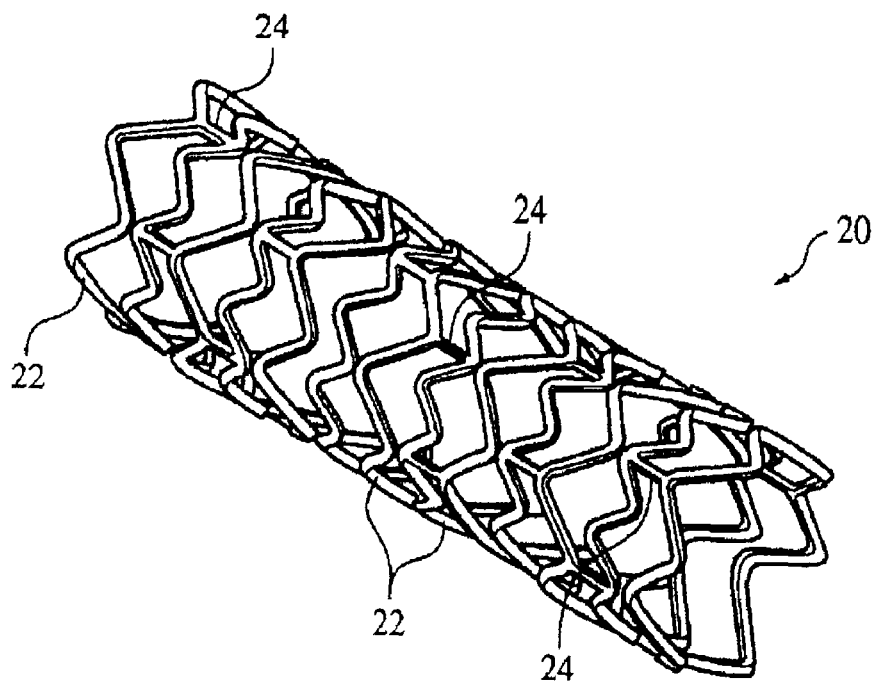
FIG. 1 is a perspective view of an embodiment of an expanded stent.

Referring to FIG. 1, a stent 20 can have the form of a tubular member defined by a plurality of bands 22 and a plurality of connectors 24 that extend between and connect adjacent bands. During use, bands 22 can be expanded from an initial, small diameter to a larger diameter to contact stent 20 against a wall of a vessel, thereby maintaining the patency of the vessel. Connectors 24 can provide stent 20 with flexibility and conformability that allow the stent to adapt to the contours of the vessel.

Figure 2:
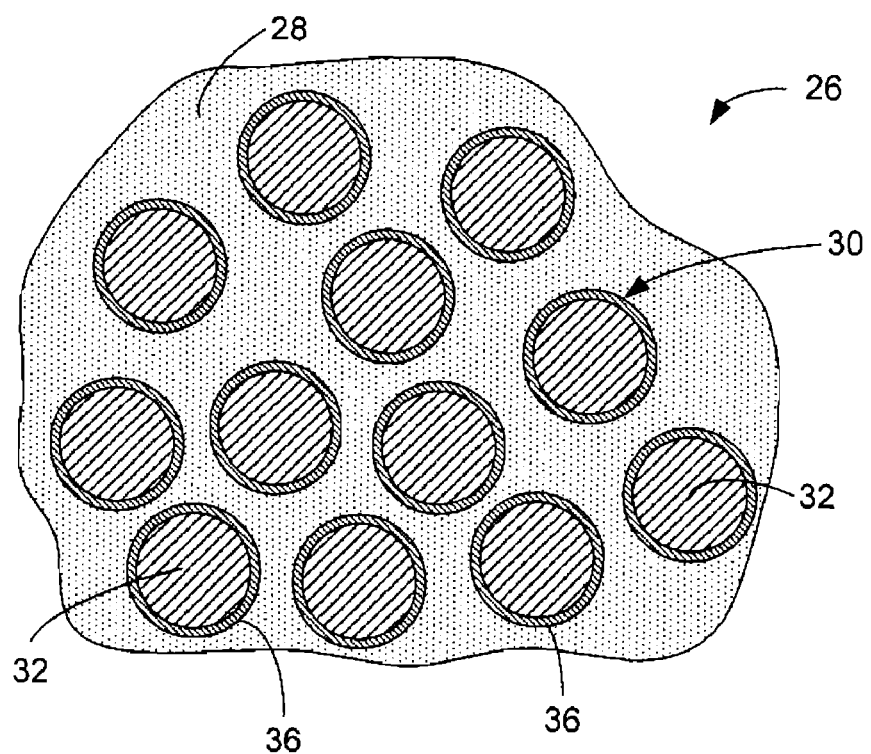
FIG. 2 is a detailed view of an embodiment of a composite.

Referring to FIG. 2, any or all of the portions of stent 20 can include a composite material 26 that features a metal matrix 28 and a plurality of stiffening particles 30 surrounded by and in the matrix 28. The stiffening particles 30 can include a metal core 32 and a thin surface layer 36. The surface layer 36 can include an oxide, carbide, nitride, or combinations thereof. The composite can include between about 10% and about 35% by weight stiffening particles 30, based upon the total weight of the composite.

Examples of suitable metals for metal matrix 28 can include titanium, niobium, tantalum, or alloys thereof. In some embodiments, the metal matrix 28 can include essentially pure titanium. In other embodiments, the metal matrix 28 can include essentially pure niobium or tantalum.

Stiffening particles 30 can have an average particle size of between 0.1 and 10 microns. They can enhance the mechanical properties of the metal matrix 28. For example, the stiffening particles 30 can increase the Young's modulus of elasticity and/or yield strength of matrix 28. The Young's modulus of elasticity of the stiffening particles 30 can be greater than the Young's modulus of elasticity of the metal matrix 28. For example, the Young's modulus of elasticity of the stiffening particles 30 can be greater than or equal to 30 Mpsi.

The metal core 32 of stiffening particles 30 can include tungsten, rhenium, molybdenum, iridium, tantalum or alloys thereof. The surface layer 36 of stiffening particles 30 can include an oxide, nitride, carbide, or combinations thereof, of the metal core 32 material. Alternatively, the surface layer 36 can include a non-native oxide such as zirconium oxide, titanium oxide, niobium oxide, iridium oxide, aluminum oxide, or chromium oxide.

The thickness of surface layer 36 can range from 1 to 100 nanometers. The surface layer 36 can inhibit diffusion of the stiffening particle metal core atoms into the metal matrix 28, thereby inhibiting the formation of alloy interfacial layers between the metal matrix 28 and the stiffening particles 30. In some embodiments, the interfacial alloy thickness between the metal matrix 28 and the stiffening particles 30 can be less than or equal to 0.1 microns when measured in any 1,000× field of view in a polished metallography cross-section viewed via backscattered electron mode in a scanning electron microscope.

The stiffening particles 30 can increase the stiffness of the metal matrix 28, resulting in a composite having good mechanical properties. For example, the composite tube 26 can have:

(a) an elongation at break of at least 12.0% or between 12 and 30%, as measured according to ASTM E8 with gage marks on a 1.0-inch gage length, 0.05 inch/minute strain rate;

(b) an ultimate tensile yield strength (YS) of 60-100 ksi, as measured according to ASTM E8;

(c) a Young's modulus of elasticity of greater than 18 Mpsi or between 18 Mpsi and 30 Mpsi, as measured according to ASTM E8; and/or (d) a density of between 4.5 g/cm$^3$ and 18.0 g/cm$^3$, as calculated from sample mass and volume measurements.

The mechanical properties that the composite provides can allow the stent to be formed with reduced wall thickness without compromising the performance of the stent. A thinner walled stent can be more easily delivered through a tortuous path, can be implanted in a smaller bodily vessel, and/or can allow more fluid flow through the stent. In some embodiments, the wall thickness of a composite layer of a finished stent made using the composite can be between 0.0015 inches and 0.0060 inches thick.

Metal cores 32 can be made by powder atomization. Other methods of making metal cores 32 for stiffening particles 30 can include bubbling of molten material, sol-gel techniques, and precursor casting.

The surface layer 36 can be created by surface treating the surface of particles made of the metal core 32 material. For example, metal powder made of the metal core 32 material can be exposed to an atmosphere having a partial pressure of oxygen, nitrogen, carbon dioxide, or combination thereof, e.g., in an atomization chamber. In some embodiments, the metal powder can be subjected to a heat treatment subsequent to atomization.

In other embodiments, the surface layer 36 can include a non-native oxide such as zirconium oxide, titanium oxide, niobium oxide, iridium oxide, or chromium oxide. Surface layers 36 of non-native oxides, or of other surface materials, can be created on metal cores 32 by any conventional coating method including, for example, plasma spraying, plating, chemical vapor deposition, sputtering, and pulsed laser deposition.

Composite 26 can be produced by blending a metal matrix powder with a plurality of stiffening particles 30, and consolidating the blend. Consolidation can be accomplished by pressing, sintering, cold compaction, hot isostatic pressing, extrusion, forging, plasma spray deposition, laser forming, or combinations thereof. The metal matrix powder can have an average particle diameter of between about 0.1 and 100 microns, and can be essentially free of surface oxides, nitrides, carbides, or other impurities.

In one embodiment, the process for preparing the composite can include blending essentially pure titanium powder, having an average particle size of between 0.1 and 100 microns, with between 10% and 35% by weight stiffening particles 30, the stiffening particles 30 having an average particle size of between 0.1 and 10 microns, and hot isostatic pressing the blend at a temperature between 1500° F. and 1700° F., and a pressure of between 10 ksi and 30 ksi, for a period of time between 1 hour and 8 hours.

Figure 3:
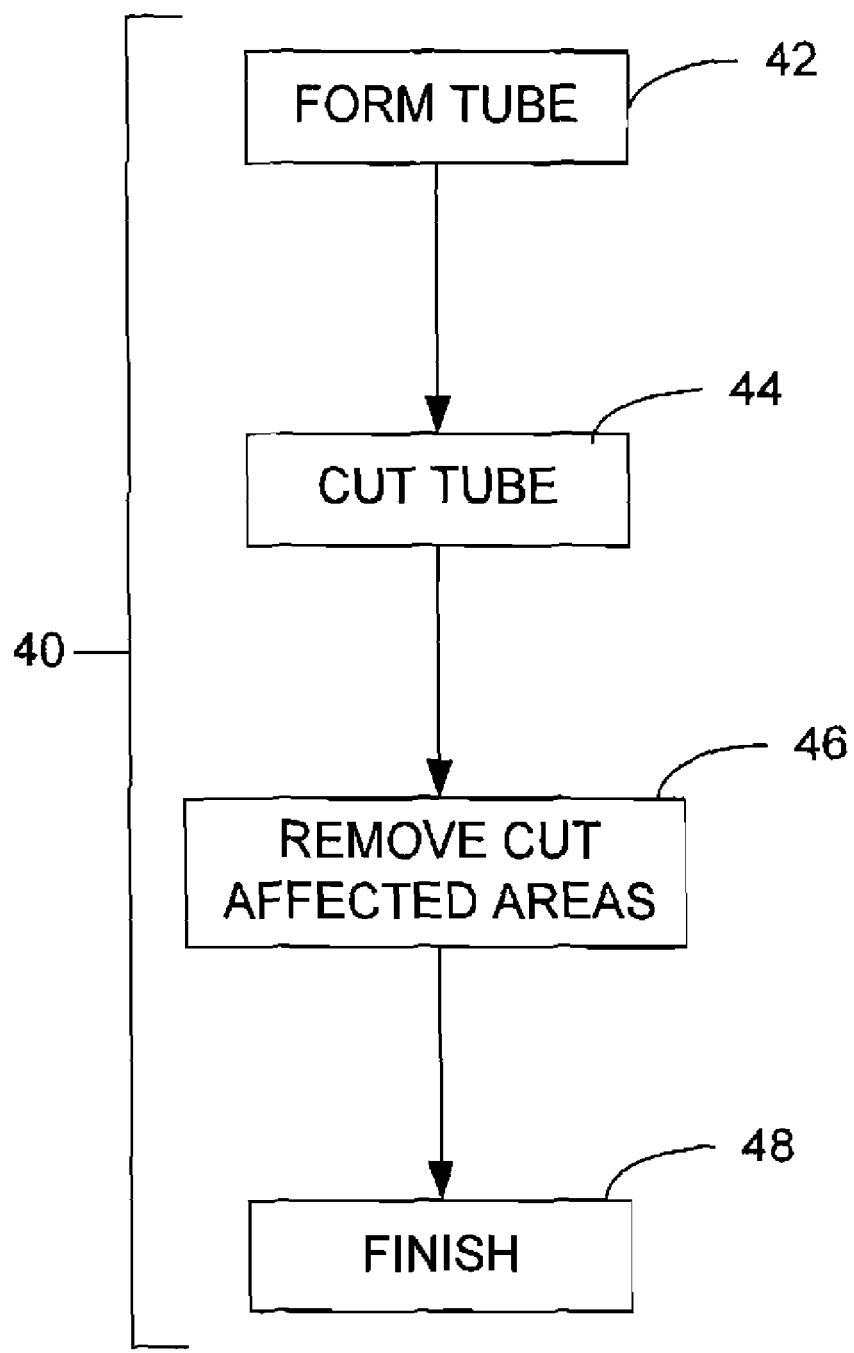
FIG. 3 is a flow chart of an embodiment of a method of making a stent.

The consolidated composite material 26 can be used to make an endoprosthesis such as a stent. FIG. 3 shows an example of a method 40 of making stent 20. As shown, method 40 can include forming a tube (step 42) including composite material 26 that makes up the tubular member of stent 20. The tube can be subsequently cut to form bands 22 and connectors 24 (step 44) to produce an unfinished stent. Areas of the unfinished stent affected by the cutting can be subsequently removed (step 46). The unfinished stent can be finished to form stent 20 (step 48).

An endoprosthesis including a composite material having variable concentrations of particles can be made by joining multiple portions (e.g., billets) of different particle concentrations by sintering. Stents with layers of composite material of different particle concentrations can be formed by sequentially adding the selected composite materials into a mold to form the tubular member.

In some embodiments, the hollow tubular member including the composite material can be drawn through a series of dies with progressively smaller circular openings to plastically deform the member to a targeted size and shape. In some embodiments, a hollow tubular member can be shaped by pilgering, fixed mandrel drawing, floating plug drawing, or a combination thereof. The resulting hollow tubular member can have an outer diameter of between 0.050 inches and 0.090 inches and a wall thickness of between 0.0030 inches and 0.0060 inches. The plastic deformation strain can harden the member (and increase its yield strength) and elongate the grains along the longitudinal axis of the member. The deformed member can be heat treated (e.g., annealed above the recrystallization temperature and/or hot isostatically pressed) to transform the elongated grain structure into an initial grain structure, e.g., one including equiaxed grains. Small or fine grains can be formed by heating the member close to the recrystallization temperature for a short time.

Large or coarse grains can be formed by heating the member at higher temperatures and/or for longer times to promote grain growth.

The resulting hollow tube can have 5% or fewer stiffening particles touching each other or in contact in series when measured in any 1,000× field of view in a polished metallography cross-section, viewed via backscattered electron mode in a scanning electron microscope. In some embodiments, the oxygen concentration in the resulting material can be less than or equal to 2000 ppm, as measured by the inert gas fusion technique.

Figure 4:
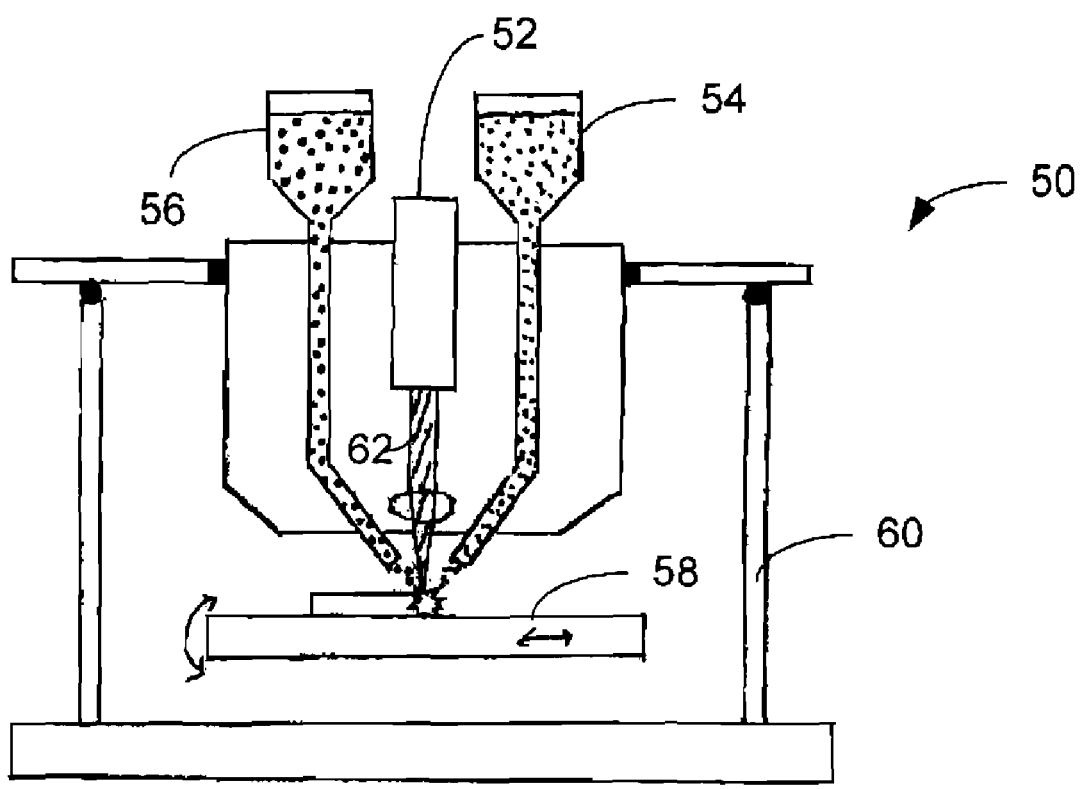
FIG. 4 is a diagrammatic view of a system for making a medical device.

Referring to FIG. 4, an example of a system 50 for making the tubular member is shown using a laser forming technique. System 50 can include a laser 52, a first hopper 54 containing a material for metallic matrix 28, a second hopper 56 containing a material for particles 30, a movable cylindrical substrate 58, and a chamber 60. Hoppers 54, 56 can be configured to selectively deliver their respective materials onto substrate 58. Laser 52 can be configured to deliver an energy beam 62 to where the materials from hoppers 54, 56 are delivered on substrate 58. Substrate 58, which can be made from a removable material such as carbon steel, cadmium, lead, magnesium, tin, and zinc, can be translated and rotated to vary the position on the substrate where the materials are deposited and energy beam 62 is addressed. Chamber 60 can be filled and purged with an inert gas to prevent oxidation or contamination of the materials. During fabrication, hoppers 54, 56 can deliver their respective material onto substrate 58, and at the same time, laser 52 can deliver sufficient energy to melt the matrix material to encapsulate the particles, thereby forming the composite material. To vary the concentrations of the matrix material and/or the particles material, the delivery rate(s) of the hopper(s) can be varied. To vary the compositions or types of particles or matrix materials, additional hoppers containing the desired materials can be used. Substrate 58 is concurrently translated and/or rotated to form a tubular member made of the composite material. In some embodiments, multiple layers of composite material can be deposited to form the resulting tubular structure. After the tubular member is made, substrate 58 can be removed by dissolution (e.g., by immersion in an acid such as nitric acid), by mechanical removal (e.g., by grinding), by melting (e.g., for substrate materials having sufficiently low melting points), and/or subliming. Laser forming is described in commonly assigned U.S. Ser. No. 10/732,492, filed on Dec. 10, 2003, and entitled "Medical Devices and Methods of Making the Same", hereby incorporated by reference.

Next, bands 22 and connectors 24 of stent 20 can be formed, as shown, by cutting the tube (step 44). Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, can flow through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above can be removed (step 46). For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing). In some embodiments, the tubular member can be near net shape configuration after step 46 is performed. "Near-net size" means that the tube has a relatively thin envelope of material that is removed to provide a finished stent. In some embodiments, the tube is formed less than about 25% oversized, e.g., less than about 15%, 10%, or 5% oversized.

The unfinished stent can then be finished to form stent 20. The unfinished stent can be finished, for example, by electropolishing to a smooth finish. Since the unfinished stent can be formed to near-net size, relatively little of the unfinished stent needs to be removed to finish the stent. As a result, further processing (which can damage the stent) and costly materials can be reduced. In some embodiments, about 0.0001 inch of the stent material can be removed by chemical milling and/or electropolishing to yield a stent. In some embodiments, the surface of the titanium composite stent would be composed of primarily titanium. Stent surface treatment can be performed by furnace, plasma, laser, or electron to convert the titanium to an oxide, nitride, carbide, or combination thereof, or the stent could be coated with other oxides, ceramics, and/or metal coatings, such as iridium oxide. A treated stent surface can enhance a healing response.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from 2 mm to 6 mm. In some embodiments, a peripheral stent can have an expanded diameter of from 5 mm to 24 mm. In certain embodiments, a gastrointestinal and/or urology stent can have an expanded diameter of from 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, self-expandable, or a combination of both (e.g., U.S. Pat. No. 5,366,504).

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

As an example, while stent 20 is shown above as being formed wholly of composite material 26, in other embodiments, the composite material forms one or more selected portions of the medical device. For example, stent 20 can include multiple layers in which one or more layers include a composite material, and one or more layers do not include a composite material. The layer(s) that includes a composite material can include the same composite material or different composite materials. The layer(s) that does not include a composite material can include one or more of the biocompatible matrix materials. The layering of the composite material provides yet another way to tailor and tune the properties of the medical device. Stents including multiple layers are described, for example, in published patent application 2004-0044397, and Heath, U.S. Pat. No. 6,287,331.

Stent 20 can be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

In some embodiments, stent 20 can be formed by fabricating a wire including the composite material, and knitting and/or weaving the wire into a tubular member.

The composite materials described herein can be used to form other endoprostheses. For example, the composite materials can be used to form a guidewire or a hypotube. A guidewire can have portions including different concentrations of particles to provide a flexible distal section for good trackability and a stiff proximal section for good pushability. The composite material can be used to form medical implants, such as hip stems and knee trays. The composite material can be used to form metal staples and wires used for wound closure so that they can be compatible with imaging techniques.

All publications, references, applications, and patents referred to herein are incorporated by reference in their entirety.

Other embodiments are within the claims.

What is claimed is:

1. An endoprosthesis comprising a composite, the composite comprising:
   (a) a metal matrix that includes a metal selected from the group consisting of titanium, niobium, tantalum, and alloys thereof; and
   (b) a plurality of discrete stiffening particles dispersed in the matrix, wherein the composite comprises between 10 and 35% by weight of the stiffening particles, based upon the weight of the composite,
   wherein the stiffening particles comprise a metal core selected from the group consisting of tungsten, iridium, rhenium, molybdenum, tantalum, and alloys thereof and a thin surface layer selected from the group consisting of oxides, carbides, nitrides, and combinations thereof.

2. The endoprosthesis of claim 1, wherein the metal matrix comprises titanium.

3. The endoprosthesis of claim 1, wherein the surface layer comprises an oxide.

4. The endoprosthesis of claim 3, wherein the oxide comprises a non-native oxide.

5. The endoprosthesis of claim 1, wherein the stiffening particles have an average particle size ranging from 0.1 μm to 10 μm.

6. The endoprosthesis of claim 1, wherein the composite has a Young's modulus of elasticity of at least 18 Mpsi.

7. The endoprosthesis of claim 1, wherein the composite has a Young's modulus of elasticity of between 18 Mpsi and 30 Mpsi.

8. The endoprosthesis of claim 1, wherein the composite has a yield strength of between 60 and 100 ksi.

9. The endoprosthesis of claim 1, wherein the composite has a percent elongation at break of 12-30%.

10. The endoprosthesis of claim 1, wherein the composite has a density of 4.5-18.0 g/cm$^3$.

11. The endoprosthesis of claim 1, wherein the endoprosthesis is a stent.

12. The endoprosthesis of claim 11, wherein the composite has a wall thickness of between about 0.0015 inches and about 0.0060 inches.

13. The endoprosthesis of claim 11, wherein the stent comprises a plurality of bands.

14. The endoprosthesis of claim 13, wherein the stent comprises a plurality of connectors connecting the plurality of bands.

15. The endoprosthesis of claim 1, wherein the thickness of the surface layer is between 1 and 100 nm.

16. An endoprosthesis comprising a composite, the composite comprising:
   (a) a metal matrix that includes a metal selected from the group consisting of titanium, niobium, tantalum, and alloys thereof; and
   (b) a plurality of discrete stiffening particles dispersed in the matrix, wherein the composite comprises between 10 and 35% by weight of the stiffening particles, based upon the weight of the composite,
   wherein the stiffening particles comprise a metal core and a thin surface layer selected from the group consisting of oxides, carbides, nitrides, and combinations thereof and have a Young's modulus of elasticity of at least 30 Mpsi.

17. The endoprosthesis of claim 1, wherein the endoprosthesis is a stent,
   wherein the composite has a Young's modulus of elasticity of at least 18 Mpsi, a yield strength of 60-100 ksi, a percent elongation to break of 12-30%, and a density of 4.5-18.0 g/cm$^3$.

18. An endoprosthesis comprising a composite, the composite comprising:
   (a) a metal matrix that includes a metal selected from the group consisting of titanium, niobium, tantalum, and alloys thereof; and
   (b) 10 and 35% by weight, based upon the weight of the composite, of discrete stiffening particles dispersed in the matrix,
   wherein the stiffening particles comprise a metal core selected from the group selected from the group consisting of tungsten, iridium, rhenium, molybdenum, tantalum, and alloys thereof and a thin surface layer comprising a non-native oxide.

19. The endoprosthesis of claim 18, wherein the metal matrix comprises titanium.

20. The endoprosthesis of claim 18, wherein the stiffening particles have an average particle size ranging from 0.1 μm to 10 μm.

21. The endoprosthesis of claim 18, wherein the composite has a Young's modulus of elasticity of between 18 Mpsi and 30 Mpsi, a yield strength of between 60 and 100 ksi, a percent elongation at break of 12-30%, and a density of 4.5-18.0 g/cm$^3$.

22. The endoprosthesis of claim 18, wherein the endoprosthesis is a stent.

23. The endoprosthesis of claim 18, wherein the thickness of the surface layer is between 1 and 100 nm.

* * * * *